(12) United States Patent
Oudry et al.

(10) Patent No.: US 8,846,014 B2
(45) Date of Patent: Sep. 30, 2014

(54) MAKEUP COMPOSITION COMPRISING A BLACK COLOUR MIXTURE OF PIGMENTS

(71) Applicant: LVMH Recherche, Saint Jean de Braye (FR)

(72) Inventors: Patrick Oudry, Mardie (FR); Myriam Chevalier, Boigny sur Bionne (FR); Emilie Gombart, Orleans (FR)

(73) Assignee: LVMH Recherche, Saint Jean de Braye (FR)

( * ) Notice: Subject to any disclaimer, the term of this patent is extended or adjusted under 35 U.S.C. 154(b) by 0 days.

(21) Appl. No.: 14/165,773

(22) Filed: Jan. 28, 2014

(65) Prior Publication Data

US 2014/0140943 A1    May 22, 2014

Related U.S. Application Data

(63) Continuation-in-part of application No. 13/429,822, filed on Mar. 26, 2012, now Pat. No. 8,758,732.

(30) Foreign Application Priority Data

Mar. 31, 2011 (FR) ..................... 11 52762

(51) Int. Cl.
| | | |
|---|---|---|
| A61K 8/00 | (2006.01) | |
| A61Q 1/04 | (2006.01) | |
| A61K 8/19 | (2006.01) | |
| A61Q 1/06 | (2006.01) | |
| A61Q 19/02 | (2006.01) | |
| A61K 8/49 | (2006.01) | |
| C09B 67/22 | (2006.01) | |
| A61K 8/26 | (2006.01) | |
| A61K 8/46 | (2006.01) | |
| A61Q 1/08 | (2006.01) | |
| C09B 63/00 | (2006.01) | |
| A61Q 1/02 | (2006.01) | |
| A61Q 1/10 | (2006.01) | |
| A61Q 3/02 | (2006.01) | |

(52) U.S. Cl.
CPC ... *A61K 8/19* (2013.01); *A61Q 1/04* (2013.01); *A61Q 1/06* (2013.01); *A61Q 19/02* (2013.01); *A61K 8/4946* (2013.01); *C09B 67/0051* (2013.01); *A61K 8/26* (2013.01); *A61K 8/466* (2013.01); *A61K 2800/43* (2013.01); *A61Q 1/08* (2013.01); *C09B 63/005* (2013.01); *A61Q 1/02* (2013.01); *A61Q 1/10* (2013.01); *A61Q 3/02* (2013.01)
USPC ............................ 424/63; 424/64; 424/78.03

(58) Field of Classification Search
CPC ....... A61K 2800/43; A61K 8/19; A61K 8/26; A61K 8/466; A61K 8/4946; A61Q 1/02; A61Q 1/04; A61Q 1/06; A61Q 1/08; A61Q 1/10; A61Q 3/02; C09B 63/005; C09B 67/0051
See application file for complete search history.

(56) References Cited

U.S. PATENT DOCUMENTS

| | | |
|---|---|---|
| 5,925,150 A | 7/1999 | Ragsdale et al. |
| 6,026,207 A | 2/2000 | Reddy et al. |
| 2005/0039636 A1 | 2/2005 | Matsumoto |
| 2006/0140702 A1 | 6/2006 | Coffey-Dawe |
| 2011/0004571 A1 | 1/2011 | Parikh et al. |
| 2011/0044919 A1 | 2/2011 | Giacomoni et al. |

FOREIGN PATENT DOCUMENTS

EP    1 757 262    2/2007

*Primary Examiner* — Lezah Roberts
*Assistant Examiner* — Nannette Holloman
(74) *Attorney, Agent, or Firm* — Hamre, Schumann, Mueller & Larson, P.C.

(57) ABSTRACT

The invention relates to cosmetic compositions comprising a black color subtractive mixture consisting of one blue pigment (ferric ammonium ferrocyanide and/or ultramarine blue), at least one yellow organic pigment and at least one red organic pigment, which are mixed homogeneously, said mixture having a very dark black color.

20 Claims, No Drawings

MAKEUP COMPOSITION COMPRISING A BLACK COLOUR MIXTURE OF PIGMENTS

The invention relates to a novel mixture of pigments and their use in coloured or colouring compositions intended for makeup.

PRIOR ART

Pigments are compounds that absorb part of the visible spectrum of light, of which spectrum the wavelengths are approximately between 400 and 700 nm, and reflect the non-absorbed wavelengths (complementary spectrum) detected by the eye.

They are commonly used in pulverulent form, dispersed in bases or binders in order to be incorporated into coloured or colouring compositions (paints, inks, makeup products) which are applied to a support to which the pigment remains attached.

Depending on their chemical nature, pigments are classified as "mineral pigments", which comprise bonds with metal ions, especially in the form of oxides, or "organic pigments" which are hydrocarbon-based, often aromatic, compounds customarily incorporating at least one excitable chromophore group.

The development of novel pigments is a significant problem for many industries, who seek pigments that produce a superior visual effect with respect to hues or intensity of the colours.

The cosmetic industry more particularly seeks novel pigments that can be used in makeup compositions applied to the skin, lips, nails or keratin fibres.

The black colour is especially used in cosmetic makeup compositions, such as mascaras, nail varnishes, lipsticks, or skin decoration compositions.

Many intrinsically black mineral pigments are known, such as for example treated or untreated black iron oxides, carbon blacks, titanium oxides, which are very commonly used for colouring compositions to which it is desired to give a black colour.

There is however, in theory, another possibility of producing a pigmentary black colour, by mixing coloured pigments, which makes use of the principle of "subtractive colour synthesis" that applies for opaque bodies such as pigments.

According to the subtractive model, the coloured pigments mix while absorbing more and more light, the mixture produced itself being of darker colour.

Thus, according to this model, it is possible in theory to obtain the colour black by mixing pigments which, once combined, absorb all the wavelengths of the visible spectrum.

Of course, as explained previously, due to the availability on the market of many pigments that are pure, of mineral origin, and of intrinsic black colour, it is not economically advantageous to straightaway use mixtures of pigments to produce this colour.

Furthermore, the preparation of a mixture of pigments exhibits difficulties of reproducibility when it is sought to obtain the colour that is exactly desired (obtaining a dark brown instead of a black), and risks of incompatibilities and/or of instability which may adversely affect the hue of the colour resulting from the mixture.

Finally, it may be particularly advantageous to have black pigments that produce a black colour at least as intense as carbon black so as to be able to substitute it in cosmetic compositions. Indeed, carbon black is in the form of nanoscale particles that may present a risk of passing through the skin barrier.

Having a mixture of pigments that produce a very intense black colour makes it possible to envisage the substitution of this nanoscale pigment into all the cosmetic compositions for making up or caring for the skin, lips or keratin fibres.

PURPOSES OF THE INVENTION

One purpose of the present invention is to solve all of the technical problems described above.

The present invention especially aims to provide a novel black mixture obtained by mixing organic red and yellow pigments with one specific blue inorganic pigment. The present invention also deals with coloured or colouring cosmetic compositions comprising this mixture.

The present invention also aims to provide make-up compositions having an improved visual effect.

One purpose of the invention is to provide compositions that produce an intense and saturated black colour, and for which a "deeper" colour is perceived, especially with reference to the mineral pigments of the prior art, such as carbon black or an iron oxide. The inventors have found that two specific inorganic blue pigments enable one to obtain very dark black color.

This intensity may be evaluated by the low luminance value $L^*$ in the CIELAB system.

One purpose of the present invention is finally to provide a method of preparing a reproducible mixture of pigments in order to obtain the colour that is exactly desired, and to limit the risks of incompatibility and/or of instability capable of adversely affecting the hue of the colour obtained by mixing, or its intensity.

Another purpose of the invention is to solve the technical problems in a reliable and reproducible manner that can be used on an industrial scale, in particular in cosmetics.

DESCRIPTION OF THE INVENTION

The inventors of the present invention have now discovered that a mixture of organic pigments makes it possible to obtain a more intense and more saturated black colour than pure black mineral pigments used for colouring compositions, especially cosmetic compositions. This therefore constitutes a particularly important advantage for marketing such mixtures. This mixture of pigments is called a "subtractive mixture" for the purposes of the invention. Thus, in the description and examples that follow, such mixtures are defined by the generic term of "subtractive mixtures".

The subtractive mixture especially makes it possible to advantageously substitute it for nanoscale carbon black in cosmetic compositions of black colour, especially intended for making up the skin or lips.

Furthermore, due to the intensity and depth of the black colour obtained, the subtractive mixture has an unexpected advantage when it is combined in compositions with optical effect particles such as nacres, in particular white nacres.

The inventors have demonstrated that the combination of a subtractive mixture and of optical effect particles in a coloured or colouring composition makes it possible to accentuate the visual effect produced by said optical effect particles, when this effect is compared to that produced when the same optical effect particles are combined with an intrinsically black mineral pigment in the same composition.

Owing to such a subtractive mixture producing an intense black colour, it is possible to prepare compositions for making up the skin, lips, nails or keratin fibres that produce a film of a more intense and deeper black, and also an optional improved optical effect when the composition additionally comprises optical effect particles.

In the description that follows, the representation of the colours is based on the "1976 CIE L*a*b*" (CIELAB) model adopted by the International Commission on Illumination (also called the CIELAB 1976 system).

In this model, L* represents the luminance (or lightness), which makes up the "black-white" colorimetric axis on a scale ranging from the value 0 (black) to the value 100 (white). Also defined is the component a*, which represents the range of the axis extending from green (negative values of a*) to red (positive values of a*) and the component b* represents the range of the axis extending from blue (negative values of b*) to yellow (positive values of b*).

In the CIELAB system, the black colour is represented by a value of L* which tends towards 0 and values of the components a* and b* which are customarily within an interval ranging from −5 to +5.

When it is sought to act on the intensity of the black colour or its depth, it is the luminance parameter L* that should more particularly be studied. A value of L* that tends towards 0 (more intense black colour) results in a more intense absorption of the wavelengths of the visible spectrum of incident light by the material illuminated.

DETAILED DESCRIPTION OF THE INVENTION

The invention relates in particular to a subtractive mixture of black colour comprising a mixture of a blue inorganic pigment, a red organic pigment and a yellow organic pigment. This mixture has a low luminance so much so that it advantageously makes it possible for the optical effects of pigments with which it may be combined in a makeup composition to stand out. The expression "organic" means containing mainly carbon and hydrogen.

The mixture advantageously has a luminance value L*(15°) of less than 30. L*(15°) represents the value of the luminance L* in the CIELAB 1976 system. It is calculated from the measurement of intensity of light reflected at an angle of 15° relative to the specular light according to the method that consists in illuminating a film comprising said subtractive mixture applied to a black background, using an incident light at 45° relative to the horizontal plane.

The "specular light" corresponds to the component of light resulting from the direct reflection of an incident light source on a surface or an object. In the present case, it represents the component of the light reflected by the film illuminated by incident light.

Advantageously, the luminance value L*(15°), measured for the subtractive mixture according to the method above, is less than or equal to 20, more preferably still less than or equal to 10.

Advantageously, said substractive mixture has a value of the component a* of greater than 0, and a value of the component b* of greater than 0. Preferably, the value of the component a* is between 0 and 3, most preferably between 0 and 1.5. Preferably, the value of the component b* is between 0 and 3, most preferably between 0 and 1.5.

Advantageously, the subtractive mixture comprises at least one blue inorganic pigment, at least one yellow organic pigment, and at least one red organic pigment.

For the purposes of the invention, the blue colour is defined in accordance with the CIELAB system by a value of the component b* of less than 0. The red colour is defined in accordance with the CIELAB system by a value of the component a* of greater than 0, preferably of greater than +10.

The yellow colour is defined in accordance with the CIELAB system by a value of the component b* of greater than 0, preferably of greater than +5.

Typically, the blue pigment has an absorption maximum at a wavelength between 490 and 780 nm. The yellow organic pigment has an absorption maximum at a wavelength between 400 and 540 nm. The red organic pigment has an absorption maximum at a wavelength between 400 and 560 nm.

The pigments used in said mixture in fact absorb only a fraction of the wavelengths of the incident light, the unabsorbed wavelengths being reflected by the sample.

Unlike the absorption profiles of the pigments, the subtractive mixture is characterized by the absence of such an absorption maximum in the visible range (wavelengths between 400 nm and 700 nm). This particular profile, free of any characteristic peak, results from the absorption, by the sample of the subtractive mixture, of all of the wavelengths in the visible range.

All the absorption spectra are carried out on samples of pigments in the pure state that are dispersed in a liquid that does not absorb in the visible range.

According to one of its aspects, the invention relates to a cosmetic composition comprising, as a black colour pigment, a black colour mixture consisting of:

20 to 90% by weight relative to the weight of the mixture of a blue inorganic pigment, and 2 to 60% by weight relative to the weight of the mixture of at least one yellow organic pigment, 2 to 50% by weight relative to the weight of the mixture of at least one red organic pigment, the sum of the weights of the three pigments being 100%, wherein the blue inorganic pigment is at least one selected from the group consisting of ferric ammonium ferrocyanide and ultramarine blue.

The weight of the blue inorganic pigment can be 20 to 90% by weight relative to the weight of the mixture, for example 25 to 85%, 30 to 80%, 35 to 75%, 40 to 65%, 45 to 60%, or 50 to 55%.

The weight of the red pigment can be 2 to 60% by weight relative to the weight of the mixture, for example 5 to 55%, 10 to 50%, 15 to 45%, 20 to 40%, 25 to 40%, or 30 to 35%.

The weight of the yellow pigment can be 2 to 50% by weight relative to the weight of the mixture, for example 5 to 45%, 10 to 40%, 15 to 35%, 20 to 30% or 25 to 30%.

The aim of the invention is to substitute the conventional black colorants and pigments used in the make-up products, by a mixture of three pigments that provides a more intense and deep black colour. The cosmetic composition of the invention advantageously contains very little or no pigments of black color such as carbon black or black iron oxide. The content of carbon black and black iron oxide is preferably less than 0.1% by weight of the composition, most preferably less than 0.05% by weight of the composition.

According to one embodiment, the black colour subtractive mixture consists of:

26 to 33% by weight relative to the weight of the mixture of a blue inorganic pigment, and 50 to 55% by weight relative to the weight of the mixture of at least one yellow organic pigment, 15 to 20% by weight relative to the weight of the mixture of at least one red organic pigment, the sum of the weights of the three pigments being 100%.

According to another embodiment, the black colour subtractive mixture consists of:

50 to 55% by weight relative to the weight of the mixture of a blue inorganic pigment, and 37 to 42% by weight relative to the weight of the mixture of at least one yellow organic pigment, 5 to 10% by weight relative to the weight of the mixture of at least one red organic pigment, the sum of the weights of the three pigments being 100%.

The organic pigments may be naturally insoluble or else may be obtained from transparent organic dyes in a liquid medium, which are then made insoluble, in the form of lakes, from which it is recalled that they are formed of three elements, a dye, a support and a precipitant, often a cation.

The "blue" pigment is thus advantageously at least one selected from the group consisting of ferric ammonium ferrocyanide (CI 77510, CAS N°. 25869-00-5) and ultramarine blue (CI 77007, CAS N°. 57455-37-5, other Name Pigment Blue 29).

The "yellow" pigment is advantageously chosen from:
the lakes of the dye having the INCI name CI 19140 (CAS No. 1934-21-0; Trisodium 5-hydroxy-1-(4-sulphophenyl)-4-(4-sulphophenylazo)-pyrazole-3-carboxylate), advantageously an aluminium lake,
the lakes of the dye having the INCI name CI 15985 (CAS No. 2783-94-0, Disodium 6-hydroxy-5-[(Z)-(4-sulphonatophenyl)diazenyl]naphthalene-2-sulphonate), advantageously an aluminium lake,
the lakes of the dye having the INCI name CI 11380 (CAS No. 85-84-7, 1-[(E)-phenyldiazenyl]naphthalen-2-amine; 1-(phenyldiazenyl)naphthalen-2-amine), and mixtures thereof.

The yellow pigment may correspond to the pigments known as FD&C Yellow No. 5, Yellow No. 6 or FD&C Yellow No. 10.

The "red" pigment is advantageously chosen from:
the lakes of the dye having the INCI name CI 15850 (CAS No. 5858-81-1, 3-Hydroxy-4[(4-methylphenyl)azo]-2-naphthalenecarboxylic Acid), advantageously a barium lake,
the lakes of the dye having the INCI name CI 1580 (CAS No. 5281-04-9, disodium (4E)-4-[(4-methyl-2-sulphonatophenyl)hydrazono]-3-oxo-3,4-dihydronaphthalene-2-carboxylate), advantageously a calcium lake,
the lakes of the dye having the INCI name CI 45380 (CAS No. 15086-94-9, 2',4',5',7'-Tetrabromo-3',6'-dihydroxyspiro(isobenzofuran-1(3H),9'-(9H)xanthen)-3-one),
the lakes of the dye having the INCI name CI 45410A (CAS No. 13473-26-2, 2,4,5,7-Tetrabromo-3,4,5,6-tetrachlorofluorescein),
the lakes of the dye having the INCI name CI 45410 (CAS No. 18472-87-2, 3,4,5,6-tetrachloro-2-(1,4,5,8-tetrabromo-6-hydroxy-3-oxoxanthen-9-yl)benzoic acid),
the lakes of the dye having the INCI name CI 73360 (CAS No. 2379-74-0, 6,6-dichloro-4,4-dimethyl-[2,2-bibenzo[b]thiophene]-3,3-dione),
the lakes of the dye having the INCI name CI 17200 (CAS No. 3567-66-6, disodium (3E)-5-amino-4-oxo-3-(2-phenylhydrazinylidene)-3,4-dihydronaphthalene-2,7-disulfonate),
the lakes of the dye having the INCI name CI 15880 (CAS No. 6417-83-0, calcium 3-hydroxy-4-[(1-sulfonato-2-naphthyl)azo]naphthalene-2-carboxylate), and mixtures thereof.

The red pigment may correspond to the pigments known as DC Red No. 6, DC Red No. 7, DC Red No. 21, DC Red No. 27, DC Red No. 28, DC Red No. 30, DC Red No. 33 or DC Red No. 34.

In one embodiment, the black colour mixture consists of:
15 to 20% by weight of a red organic pigment, preferably of a lake, advantageously a calcium lake, of the dye having the INCI name CI 1580 (CAS No. 5281-04-9, disodium (4E)-4-[(4-methyl-2-sulphonatophenyl)hydrazono]-3-oxo-3,4-dihydronaphthalene-2-carboxylate), also known as DC Red No. 7, 50 to 55% by weight of a yellow organic pigment, preferably of a lake, advantageously an aluminium lake, of the dye having the INCI name CI 19140 (CAS No. 1934-21-0; Trisodium 5-hydroxy-1-(4-sulphophenyl)-4-(4-sulphophenylazo)pyrazole-3-carboxylate), also known as FD&C Yellow No. 5, and 26 to 33% by weight of ferric ammonium ferrocyanide.

In another embodiment, the black colour mixture consists of:
5 to 10% by weight of a red organic pigment, preferably of a lake, advantageously a calcium lake, of the dye having the INCI name CI 1580 (CAS No. 5281-04-9, disodium (4E)-4-[(4-methyl-2-sulphonatophenyl)hydrazono]-3-oxo-3,4-dihydronaphthalene-2-carboxylate), also known as DC Red No. 7, 37 to 42% by weight of a yellow organic pigment, preferably of a lake, advantageously an aluminium lake, of the dye having the INCI name CI 19140 (CAS No. 1934-21-0; Trisodium 5-hydroxy-1-(4-sulphophenyl)-4-(4-sulphophenylazo)pyrazole-3-carboxylate), also known as FD&C Yellow No. 5, and 50 to 55% by weight of ferric ammonium ferrocyanide.

One particular aspect of the invention lies in the production of an intense black, also referred to by a person skilled in the art as "deep black" without incorporating carbon black into the composition. Generally, the compositions that make it possible to produce an intense black or deep black comprise the use of carbon black, in particular in the form of nanoscale particles. However these particles pose the problem of skin penetration or even pulmonary penetration that are obviously to be avoided. The present invention avoids this technical problem via the use of an intense or deep black pigment without the use of carbon black. Thus, according to one preferred variant, the compositions of the invention do not comprise carbon black, and in particular do not comprise nanoscale particles of carbon black.

The subtractive mixture of black colour is advantageously dispersed in a support medium.

Typically, the cosmetic compositions according to the invention are in the form of mascara, blusher, nail varnish, lipstick, gloss, eyeliner, foundation, eye shadow, or skin decoration compositions (especially anhydrous compositions or emulsions). Among the compositions that may advantageously comprise the black subtractive mixture, mention may be made of cosmetic compositions, more particularly of eye make-up compositions such as mascaras.

One advantageous support medium may be translucent or transparent, especially for a nail varnish or a lipstick.

The term "translucent" means "that allows light to pass through without making it possible to distinguish objects".

The term "transparent" means "which allows light to pass through, and makes it possible to distinguish objects".

Advantageously, the composition is a cosmetic composition comprising a cosmetically acceptable medium in which the subtractive mixture is dispersed.

According to one preferred embodiment, the composition comprises from 1% to 80% by weight of the subtractive mixture.

The medium in which said subtractive mixture may be dispersed may be solid, and especially pulverulent, pasty, liquid or semi-liquid.

The composition according to the present invention is not itself particularly limited in the compounds that it comprises.

It may comprise any type of compound or mixture of compounds, if it is acceptable for the type of compositions in which it is incorporated. These compounds are suitable for the desired functional properties (viscosity, texture for example) of the composition and for the use which is made of the composition.

In the case of cosmetic compositions, it is necessary for these compounds to be cosmetically acceptable, that is to say suitable to be brought into contact with human skin, the lips, nails or keratin fibres without toxicity, incompatibility, allergic response or equivalent, going beyond acceptable qualitative and/or quantitative tolerances. This contacting is carried out directly or indirectly, and generally by simple topical application.

Advantageously, the composition comprises exclusively the subtractive mixture for colouring said composition.

However, it is possible to obtain a particularly surprising visual effect when the subtractive mixture is combined in a composition with at least one "optical effect" (or optically active) material.

Indeed, as explained previously, once applied to the skin, lips, nails or keratin fibres, the composition comprising the combination produces such an intense and saturated black colour that it makes it possible for the effect produced by the optically active material to stand out.

The composition according to the invention thus advantageously comprises at least one "optical effect" material chosen from reflective particles, goniochromatic colouring agents such as nacres or nacreous or interference pigments, and any mixture thereof.

The expression "reflective particles" denotes particles having a size, structure and surface finish that enables them to reflect incident light with sufficient intensity to create bright points on the surface of the composition, when the latter is applied to the surface to be made up.

The reflective particles may be chosen from particles having a natural or synthetic substrate coated at least partially with at least one layer comprising at least one metal or a metallic compound such as a metal oxide.

The substrate may be chosen from glasses, ceramics, graphite, metal oxides, aluminas, silicas, silicates, especially aluminosilicates and borosilicates, and synthetic mica.

The layer coating the substrate may comprise a metal advantageously chosen from Ag, Au, Cu, Al, Ni, Sn, Mg, Cr, Mo, Ti, Pt, Va, Rb, W, Zn, Ge, Te, Se and alloys thereof. Ag, Au, Al, Zn, Ni, Mo, Cr, Cu and alloys thereof (for example bronzes and brasses), or at least one metallic compound, especially a metal oxide, for example chosen from titanium oxides, especially $TiO_2$, iron oxides especially $Fe_2O_3$, tin oxides, chromium oxides, barium sulphate and the following compounds: $MgF_2$, $CrF_3$, ZnS, ZnSe, $SiO_2$, $Al_2O_3$, MgO, $Y_2O_3$, $SeO_3$, SiO, $HfO_2$, $ZrO_2$, $CeO_2$, $Nb_2O_5$, $Ta_2O_5$, $MoS_2$ and mixtures or alloys thereof.

According to one particular embodiment, the composition of the invention advantageously comprises at least one nacre of natural or synthetic origin and/or at least one nacreous or interference pigment, which may have numerous variations in colour or reflection, particularly as a function of the observation angle.

Natural nacre arises from successive depositions of calcium carbonate inside freshwater or saltwater shells such as pearl oysters.

Nacreous pigments are advantageously in the form of a support covered with one or more layers of coating such as those of (support/coating) structure:

natural mica/titanium oxide ($TiO_2$)
natural mica/$TiO_2$/iron oxide or carmine
natural mica/$TiO_2$/organic pigment
natural mica/bismuth oxychloride/iron oxide
synthetic mica/$TiO_2$
synthetic mica/$TiO_2$/iron oxide or carmine
synthetic mica/$TiO_2$/organic pigment
calcium sodium borosilicate/iron oxide
calcium sodium borosilicate/$TiO_2$
calcium sodium borosilicate/$TiO_2$/iron oxide
calcium aluminium borosilicate/$TiO_2$/iron oxide
glass platelets/$TiO_2$/tin oxide
glass platelets/$TiO_2$/iron oxide or carmine
glass platelets/$TiO_2$/organic pigment
glass platelets/silver
aluminium/silica
aluminium/silica/silver/tin oxide
silica/$TiO_2$
silica/iron oxide
mica/bismuth oxychloride, or else in the form of liquid crystals or of multilayer polymer films comprising, for example, one or more polyethylene terephthalate copolymers, ethylene/vinyl acetate copolymers and acrylate copolymers.

By way of example for illustrating the invention, mention may especially be made of the nacres, nacreous or interference pigments consisting of a mica support coated with layers based on metal (iron, titanium, tin, etc.) oxides, sold by the company Eckart under the name Prestige®, or else sold by the company BASF under the names Cloisonne®, Timica or Flamenco®, or else sold by the company Merck under the name Colorona®, the nacres or nacreous or interference pigments consisting of a calcium sodium borosilicate support coated with successive layers based on metal oxides sold by the company Eckart under the name Mirage® or by the company BASF under the name Reflecks or those consisting of a calcium aluminium borosilicate support coated with successive layers based on metal oxides sold by the company Merck under the name Ronastar®.

For these nacres, nacreous or interference pigments, the number of layers and the composition of each layer, especially as regards the metal oxides, are developed so as to obtain various hues and colour reflections depending on the observation angle.

Advantageously, the composition comprising an "optical effect" material is a cosmetic makeup composition such as those mentioned previously.

The composition of the invention also advantageously comprises from 0 to 4% by weight of an interference or nacreous pigment, preferably a white transparent nacreous pigment.

The composition of the invention also advantageously comprises a binder, used for aiding in the dispersion of the subtractive mixture in the medium of the composition and in attaching the composition to the support to which it is applied, and optionally at least one film-forming agent.

The binder may be of synthetic or natural origin, and may especially be chosen from polymers or copolymers, optionally capable of forming films, fatty substances such as oils or waxes, or else solid fillers.

The polymers or copolymers may be chosen from those which are available to a person skilled in the art.

They may be chosen from lipophilic polymers or copolymers, such as for example alkyl celluloses, especially ethyl cellulose or propyl cellulose, vinyl ester copolymers, polyalkylenes such as polybutene, copolymers of vinylpyrrolidone (VP), especially copolymers of vinylpyrrolidone and an alkene, such as the VP/eicosene, VP/hexadecene, VP/triacontene, VP/styrene and VP/acrylic acid/lauryl methacrylate copolymers, silicone resins, and mixtures thereof.

They may also be chosen from hydrophilic polymers or copolymers such as for example proteins, especially proteins of plant origin such as wheat or soybean proteins; proteins of animal origin such as keratins, sulphonic proteins, polymers derived from cellulose, especially hydroxyethyl cellulose, hydroxypropyl cellulose, methyl cellulose, ethyl hydroxyethyl cellulose, carboxymethyl cellulose, acrylic polymers or copolymers, especially polyacrylates or polymethacrylates, vinyl polymers such as polyvinylpyrrolidones, copolymers of vinylpyrrolidone and vinyl acetate; copolymers of vinylpyrrolidone and of caprolactam; polyvinyl alcohol, chitin or chitosan polymers, gum arabic, guar gum, xanthan derivatives, gum karaya, alginates, carrageenans, glycoaminoglycans, hyaluronic acid and its derivatives or else shellac resin, and mixtures thereof.

The function of these polymers or copolymers differs depending on the type of composition. They are, for example, used for modifying the viscosity, the consistency or the texture of the composition or else are chosen for their ability to form a film at the time that the composition is applied to a support, as is the case, for example, for a cosmetic composition applied to the skin, lips, nails or keratin fibres.

The composition of the invention thus advantageously comprises at least one film-forming polymer or copolymer, advantageously used in combination with adjuvants such as coalescing agents or plasticizers, the role of which is to improve the formation of the film, its plasticity and its strength once applied to and dried on the support.

The composition of the invention may additionally comprise one or more fatty substances chosen by a person skilled in the art on the basis of his general knowledge, especially for helping to disperse the subtractive mixture, or to improve the consistency and/or texture of the composition.

These fatty substances may be of animal, plant, mineral or synthetic origin.

They are especially advantageously chosen from oils, waxes or else pasty fatty substances.

For the purposes of the present invention, the term "oil" is understood to mean a compound that is liquid at room temperature (25° C.) and atmospheric pressure (1,013.25 hPa), and which is insoluble in water or is soluble to less than 10% by weight relative to the weight of oil introduced into the water at 25° C.

The term "wax" is understood to mean a fatty substance having a reversible liquid-solid change in state, which has a melting point above 30° C. and generally below 90° C., and which has, in the solid state, an anisotropic crystalline arrangement.

The expression "pasty fatty substance" is understood to mean a lipophilic fatty compound having a reversible solid/liquid change in state, which has, in the solid state, an anisotropic crystalline arrangement, and which comprises, at a temperature of 23° C., a liquid fraction and a solid fraction.

The composition may also comprise powders which may constitute a solid filler.

The composition may especially comprise powders that have been pretreated in order to modify the shape and/or surface finish of the particles constituting said powders, and/or so as to modify the visual and/or sensory properties thereof, and/or to modify the behaviour thereof, especially during the preparation of cosmetic compositions in which they are used.

The treatment of these powders may consist of a partial or complete coating of the particles using substances such as amino acids, silicones such as dimethicone, metal salts or collagen.

The particles advantageously have a mean diameter of greater than 100 nm and up to 200 µm, and more particularly a diameter between 10 and 100 µm.

The composition is advantageously in solid form, and especially pulverulent, pasty, liquid or semi-liquid form.

The composition according to the invention is advantageously a cosmetic composition, and more particularly a composition for making up or caring for the skin, lips, nails or keratin fibres.

The cosmetic composition of the invention is advantageously a mascara, a blusher, a nail varnish, a lipstick, a gloss, an eyeliner, a foundation, an eye shadow or a skin decoration composition (anhydrous composition or emulsion).

The cosmetic composition is advantageously of black colour and/or is intended to produce such a colour after it is applied to the skin, lips, nails or keratin fibres, especially the eyelashes or eyebrows.

Such a composition is advantageously free of nanoscale carbon black.

The cosmetic composition may also be constituted only partly of a composition of black colour, for example pressed powders of various colours such as a foundation or eye shadow, in which the black colour is obtained using the subtractive mixture.

The total amount of subtractive mixture in a cosmetic composition intended for makeup differs depending on the type of composition and the applications thereof.

A composition of nail varnish type customarily comprises from 0.1 to 6% by weight of pigment(s) relative to the total weight of the composition.

A composition of lipstick type customarily comprises from 0.1 to 15% by weight of pigment(s) relative to the total weight of the composition.

A composition of gloss type customarily comprises from 0.1 to 8% by weight of pigment(s) relative to the total weight of the composition.

A composition of loose or pressed powders (eye shadows) type customarily comprises from 0.1 to 30% by weight of pigment(s) relative to the total weight of the composition.

A composition of foundation type customarily comprises from 0.1 to 15% by weight of pigment(s) relative to the total weight of the composition.

The percentages are given here by way of example, however it is possible to prepare compositions for which the percentage may differ from that indicated above, without this adversely affecting the stability or the visual appearance of the product.

According to one particularly preferred embodiment, the cosmetically acceptable medium in which the subtractive mixture is dispersed is translucent or transparent.

The excipients forming the medium are solubilized and/or dispersed in a solvent so as to form a translucent or transparent phase in which the subtractive mixture is dispersed. Said phase is also referred to as a "cosmetic base" in the present invention.

Thus, the invention covers, according to one particular aspect, a makeup composition comprising a translucent or transparent cosmetic base in which the subtractive mixture is dispersed, and optionally at least one "optical effect" material.

Such a composition is especially a nail varnish formed of a translucent or transparent base that itself advantageously comprises at least one film-forming agent such as for example nitrocellulose, at least one plasticizer and at least one rheology additive, these compounds being solubilised and/or dispersed in a solvent or a solvent mixture such as for example butyl acetate and/or ethyl acetate.

The cosmetic composition according to the invention may also comprise one or more cosmetic active agents especially chosen from moisturizers or humectants, antiageing agents, antimicrobial agents or else screening agents that protect against UV radiation.

These active agents may be of natural or synthetic origin, and may especially be in the form of an extract of a plant or of a part of a plant, of a solution of said extract or of a molecule that is synthesized or isolated from one of these extracts.

The extract may be obtained from any cosmetically acceptable extraction process, and especially via a process using a polar solvent or a mixture of polar solvents especially chosen from water, alcohols comprising from 1 to 6 carbon atoms, or else glycols.

The cosmetic composition according to the invention may lastly comprise one or more excipients chosen from preservatives, antioxidants, fragrances, surfactants and rheology additives.

Another subject of the invention targets a process for preparing a composition as described previously, said process being wherein it comprises a step of preparing a dispersion of the subtractive mixture in a support medium, and optionally a milling step.

According to one preferred embodiment, said dispersion of subtractive mixture is prepared by separately predispersing each pigment in said medium, these dispersions then being themselves mixed in proportion.

It is possible to carry out a simple mixing of the pigments in order to form the subtractive mixture and to disperse, if necessary, the subtractive mixture in order to prepare a suitable composition.

Advantageously, said medium comprises at least one binder and optionally at least one film-forming agent.

The process may thus comprise a first step in which said advantageously translucent or transparent medium is prepared, especially by putting a film-forming agent into solution in a solvent.

The process may additionally comprise a step of mixing at least one "optical effect" material into said dispersion of the subtractive mixture.

Another subject of the invention targets a cosmetic care or makeup process wherein it comprises the application of a cosmetic composition as defined previously or prepared according to the process described previously in order to obtain a makeup effect on the skin, lips, nails or keratin fibres.

Other purposes, features and advantages of the invention will become clearly apparent to a person skilled in the art after reading the description and examples which are given by way of illustration and cannot therefore in any way limit the scope of the invention.

In the examples, all the percentages are given by weight, unless otherwise indicated, and the temperature is expressed in degrees Celsius unless otherwise indicated, and the pressure is atmospheric pressure, unless otherwise indicated.

EXAMPLES

Example 1

Dispersion of the Subtractive Mixture

Dispersions were prepared comprising the subtractive mixture of black colour according to the formulae below (% by weight relative to the final mixture):

Black 1 Mixture
31.4% of ferric ammonium ferrocyanide (CI 77510)
51.7% of an aluminium lake of the dye FD&C Yellow No. 5 (CI 19140)
16.9% of a calcium lake of the dye DC Red No. 7 (CI 15850)

Black 2 Mixture
28% of ferric ammonium ferrocyanide (CI 77510)
54% of an aluminium lake of the dye FD&C Yellow No. 5 (CI 19140)
18% of a calcium lake of the dye DC Red No. 7 (CI 15850)

Black 3 Mixture
52% of ferric ammonium ferrocyanide (CI 77510)
40% of an aluminium lake of the dye FD&C Yellow No. 5 (CI 19140)
8% of a calcium lake of the dye DC Red No. 7 (CI 15850)

Each pigment constituting the BLACK mixture was first dispersed at 4% by weight in a transparent nail varnish base (VARNISH BASE 1) essentially consisting of a film-forming polymer such as nitrocellulose, at least one plasticizer and at least one rheology additive, in a solvent or mixture of solvents (butyl acetate and/or ethyl acetate). The resulting dispersion is worded "BLACK mixture dispersion".

Every dispersion was homogenized using a Rayneri deflocculator. The three dispersions were mixed together in the indicated ratios. A dispersion of black colour was thus obtained, containing 4% by total weight of pigments.

The values of $L^*(15°)$ measured for the subtractive mixtures are supposed to be less than 20. The intensity and saturation of the black colour of the compositions comprising a subtractive mixture should be significantly superior to those obtained for black iron oxiden and carbon black.

Example 2

Nail Varnish

A nail varnish was prepared with the VARNISH BASE 1 and the BLACK mixture dispersion containing the BLACK 1 mixture of Example 1.

| | |
|---|---|
| VARNISH BASE 1 | 91.6 |
| BLACK mixture dispersion of example 1 containing BLACK mixture 1 | 5.2 |
| Nacres | 3.2 |

Example 3

Nail Varnish

A nail varnish was prepared with a VARNISH BASE 2 and the BLACK mixture dispersion containing the BLACK 2 mixture of Example 1.

The VARNISH BASE 2 was a transparent nail varnish base essentially consisting of a film-forming polymer such as nitrocellulose, at least one plasticizer and at least one rheology additive, in a solvent or mixture of solvents (butyl acetate and/or ethyl acetate).

| | |
|---|---|
| VARNISH BASE 2 | 50% |
| BLACK mixture dispersion of example 1 containing BLACK mixture 2 | 50% |

Example 4

Nail Varnishes

Five nail varnishes were prepared with a VARNISH BASE 3 and a BLACK mixture dispersion of Example 1, according to the ratios bellow. Nacres gave many tints, such as bronze, ink, greyish, duck or steel.

The VARNISH BASE 3 was a transparent nail varnish base essentially consisting of a film-forming polymer such as nitrocellulose, at least one plasticizer and at least one rheology additive, in a solvent or mixture of solvents (butyl acetate and/or ethyl acetate).

| | |
|---|---|
| VARNISH BASE 3 | 49-49.5% |
| BLACK mixture dispersion of example 1 containing BLACK 3 mixture or BLACK 1 mixture | qsp 100% |
| Nacres | 0-2% |

Example 5

Mascara

A mascara can be prepared that is in the form of a transparent base in which one of the black colour subtractive mixtures from Example 1 was dispersed.

The mascara can have the following formula (% by weight):

| | |
|---|---|
| Subtractive mixture of example 1 | 12 |
| 1,3-butylene glycol | 10 |
| Glycerol | 20.5 |
| Film-forming acrylic polymer | 12 |
| Phenoxyethanol | 0.5 |
| Mica | 9 |
| Water | 36 |

The application as a film onto the eyelashes, of the mascara formed by a transparent base in which the subtractive mixture is dispersed can produce an intense visual effect, especially due to the intensity of the colour.

Example 6

Composition for the Lips

The composition can be in the form of a lipstick and comprise one of the subtractive mixtures from Example 1 dispersed in a transparent base.

The composition can have the following formula (% by weight):

| | |
|---|---|
| Subtractive mixture of example 1 | 5.5 |
| Polymer of ATPA * type | 16.5 |
| Ethylhexyl hydroxystearate | 12 |
| Hydrogenated polyisobutene | 55 |
| Cetyl alcohol | 3.2 |
| Hydrogenated styrene/methylstyrene/indene copolymer | 7 |
| Dibutyl lauroyl glutamide | 0.8 |

* INCI = Bis-Dioctadecylamide Dimer Dilinoleic Acid/Ethylenediamine Copolymer.

The composition can be formed from an anhydrous transparent base in which the substractive mixture is dispersed. The composition can be applied as a film to the lips in order to produce an intense black effect.

Example 7

Mascara

The mascara below can be formed from an opaque base emulsified in water. Its formula was the following (% by weight):

| | |
|---|---|
| Subtractive mixture of of example 1 | 15 |
| Paraffin | 17 |
| Hydroxyethyl cellulose | 1.3 |
| Gum arabic | 1.7 |
| Triethanolamine | 2.2 |
| Palmitic acid | 2.2 |
| Stearic acid | 2.2 |
| Bis-Diglyceryl Polyacyladipate-2 | 2.3 |
| C18-36 triglycerides | 3.0 |
| Waxes | 4.5 |
| Preservatives | 2.0 |
| Purified water | qs 100 |

The mascara, once applied as a film to the eyelashes using an applicator, can form a film of an intense and covering black.

Example 8

Composition for Body Makeup

The composition can have the following formula (% by weight)

| | |
|---|---|
| Subtractive mixture of example 1 | 11 |
| Wax | 4 |
| Vinylpyrrolidone/triacontene copolymer | 4 |
| Vinylpyrrolidone/eicosene copolymer | 4 |
| Thickener | 7 |
| Filler | 1 |
| Volatile hydrocarbon-based oils | qs 100 |

The composition can be applied to the skin using a brush or an equivalent device enabling a homogeneous and precise application. The black film can form withstood the rubbing of clothing against the skin and produce an intense black colour.

The invention claimed is

1. A composition comprising, as a black colour pigment, a black colour mixture consisting of:
   20 to 90% by weight relative to the weight of the mixture of a blue inorganic pigment,
   2 to 60% by weight relative to the weight of the mixture of at least one yellow organic pigment, and
   2 to 50% by weight relative to the weight of the mixture of at least one red organic pigment, the sum of the weights of the three pigments being 100%,
   wherein the blue inorganic pigment is at least one selected from the group consisting of ferric ammonium ferrocyanide and ultramarine blue.

2. The composition according to claim 1, wherein said mixture is dispersed in a translucent or transparent liquid support medium.

3. The composition according to claim 1, wherein the organic pigments are lakes of organic dyes.

4. The composition according to claim 1, wherein:
   the blue inorganic pigment is selected from the group consisting of ferric ammonium ferrocyanide and ultramarine blue,
   the yellow organic pigment is selected from the group consisting of the lakes of dye FD&C Yellow No. 5, the lakes of dye FD&C Yellow No. 6, the lakes of dye FD&C Yellow No. 10, and mixtures thereof, and the red organic pigment is selected from the group consisting of the lakes of dye DC Red No. 6, the lakes of dye DC Red No. 7, the lakes of dye DC Red No. 21, the lakes of DC Red No. 27, the lakes of dye DC Red No. 28, the lakes of DC Red No. 30, the lakes of DC Red No. 33, the lakes of DC Red No. 34, and mixtures thereof.

5. The composition according to claim 1, wherein the black colour mixture consists of:
26 to 33% by weight relative to the weight of the mixture of a blue inorganic pigment, and
50 to 55% by weight relative to the weight of the mixture of at least one yellow organic pigment, and
15 to 20% by weight relative to the weight of the mixture of at least one red organic pigment.

6. The composition according to claim 1, wherein the black colour mixture consists of:
50 to 55% by weight relative to the weight of the mixture of a blue inorganic pigment,
37 to 42% by weight relative to the weight of the mixture of at least one yellow organic pigment, and
5 to 10% by weight relative to the weight of the mixture of at least one red organic pigment.

7. The composition according to claim 5, wherein the blue inorganic pigment is ferric ammonium ferrocyanide, the yellow pigment is a lake of FD&C Yellow No. 5, and the red pigment is a lake of DC Red No. 7.

8. The composition according to claim 1, comprising 1 to 4% by weight of at least one optical effect material selected from the group consisting of reflective particles and goniochromatic colouring agents.

9. The composition according to claim 1, comprising at least one nacreous pigment (1) in the form of a support covered with one or more layers of coating, (2) in the form of a liquid crystal, or (3) in the form of a multilayer polymer film.

10. The composition according to claim 9, comprising at least one nacreous pigment—in the form of a support covered with one or more layers of coating—selected from the group consisting of:
natural mica/titanium oxide ($TiO_2$)
natural mica/$TiO_2$/iron oxide or carmine
natural mica/$TiO_2$/organic pigment
natural mica/bismuth oxychloride/iron oxide
synthetic mica/$TiO_2$
synthetic mica/$TiO_2$/iron oxide or carmine
synthetic mica/$TiO_2$/organic pigment
calcium sodium borosilicate/iron oxide
calcium sodium borosilicate/$TiO_2$
calcium sodium borosilicate/$TiO_2$/iron oxide
calcium aluminium borosilicate/$TiO_2$/iron oxide
glass platelets/$TiO_2$/tin oxide
glass platelets/$TiO_2$/iron oxide or carmine
glass platelets/$TiO_2$/organic pigment
glass platelets/silver
aluminium/silica
aluminium/silica/silver/tin oxide
silica/$TiO_2$
silica/iron oxide, and
mica/bismuth oxychloride.

11. The composition according to claim 1, for making up or caring for the skin, lips, nails or keratin fibres.

12. The composition according to claim 1, in the form of a mascara, a blusher, a nail varnish, a lipstick, a gloss, an eyeliner, a foundation, an eyeshadow, or a skin decoration product.

13. The composition according to claim 2, in the form of a nail varnish wherein the translucent or transparent medium comprises at least one film-forming agent, at least one plasticizer and at least one rheology additive, these compounds being solubilized and/or dispersed in a solvent or a solvent mixture.

14. The composition according to claim 1, further comprising at least one excipient selected from the group consisting of preserving agents, antioxidants, fragrances, surfactants, rheology additives, and any mixture thereof, and optionally one or more cosmetic active agents.

15. The composition according to claim 1 that does not comprise carbon black and black iron oxide.

16. Process for preparing a cosmetic composition according to claim 1, comprising a step of preparing a dispersion of the black colour mixture in a translucent or transparent support medium.

17. Process according to claim 16, wherein the dispersion of black colour mixture is prepared by separately predispersing each pigment in said medium, these dispersions then being themselves mixed in proportion.

18. Process according to claim 16, wherein the medium comprises at least one binder and at least one film-forming agent.

19. Process according to claim 16, comprising a step of mixing at least one optical effect material in said dispersion of black colour mixture.

20. Cosmetic care method, comprising the application of a composition as defined in claim 1 to the skin and/or the keratin fibres.

* * * * *